US010718639B2

(12) United States Patent
Fuhrer

(10) Patent No.: US 10,718,639 B2
(45) Date of Patent: Jul. 21, 2020

(54) SENSOR CHIP

(71) Applicant: Sensirion AG, Stafa (CH)

(72) Inventor: Samuel Fuhrer, Richterswil (CH)

(73) Assignee: Sensirion AG, Stafa (CH)

( * ) Notice: Subject to any disclaimer, the term of this patent is extended or adjusted under 35 U.S.C. 154(b) by 986 days.

(21) Appl. No.: 14/809,429

(22) Filed: Jul. 27, 2015

(65) Prior Publication Data

US 2016/0033991 A1   Feb. 4, 2016

(30) Foreign Application Priority Data

Jul. 29, 2014 (EP) .................................... 14002639

(51) Int. Cl.
G01D 11/00 (2006.01)
G01N 33/00 (2006.01)
G06F 1/16 (2006.01)
G01N 27/00 (2006.01)
H04N 1/60 (2006.01)

(52) U.S. Cl.
CPC .......... *G01D 11/00* (2013.01); *G01N 33/0006* (2013.01); *G06F 1/16* (2013.01); *G01N 27/00* (2013.01); *H04N 1/60* (2013.01)

(58) Field of Classification Search
CPC ...... G01N 33/0006; G06F 1/16; G01R 17/00; G01D 11/00
See application file for complete search history.

(56) References Cited

U.S. PATENT DOCUMENTS

| 5,062,446 A | 11/1991 | Anderson |
| 6,621,498 B1* | 9/2003 | Handley ............... H04N 1/6019 345/601 |
| 6,744,389 B2 | 6/2004 | Haeberli et al. |
| 8,250,921 B2 | 8/2012 | Nasiri et al. |
| 2012/0304742 A1* | 12/2012 | Cummins ............ G01N 27/121 73/31.06 |
| 2013/0113507 A1 | 5/2013 | Danesh et al. |
| 2014/0076022 A1 | 3/2014 | Ohlsson et al. |
| 2014/0253102 A1* | 9/2014 | Wood .................... G01R 1/203 324/140 R |

(Continued)

FOREIGN PATENT DOCUMENTS

| CN | 103162901 | 6/2013 |
| CN | 103410501 | 11/2013 |

(Continued)

OTHER PUBLICATIONS

Tabata et al., "High-speed Rotation of Digital Images by Ranster Scanning and Table-Lookup Operaton," Systems and Computer in Japan, vol. 17, No. 11, 1986.*

(Continued)

*Primary Examiner* — Ajay Ojha
(74) *Attorney, Agent, or Firm* — Cooper & Dunham LLP

(57) ABSTRACT

A sensor chip comprises a sensing element providing a sensor signal, an on-chip memory, a configuration of a look up table of dimension N stored in the on-chip memory for assigning an output value to a combination of N input values, and a look up table engine for determining a corresponding output value in response to receiving a memory address for the look up table configuration and in response to receiving a sensor value derived from the sensor signal as one of the N input values.

16 Claims, 4 Drawing Sheets

(56) References Cited

U.S. PATENT DOCUMENTS

2014/0263399 A1\* 9/2014 Keating ............... B67D 3/0041
222/1

FOREIGN PATENT DOCUMENTS

| EP | 2762881 | 8/2014 |
|----|---------|--------|
| EP | 2763381 | 8/2014 |
| EP | 2763468 | 8/2014 |

OTHER PUBLICATIONS azosensors.com Staff Writers, Design of a MEMS Based Mass Flow Meter, Aug. 30, 2013. pp. 1-3.
Alan Richard Wilson et al., Networked Low-Power Sensing: Network Interface and Main Operating System, IEEE Sensors Journal, vol. 10, No. 9, Sep. 2010, pp. 1495-1507.
Alireza Shoa et al., Run-Time Reconfigurable Systems for Digital Signal Processing Applications; A Survey, Journal of VLSI Signal Processing 39, 2005, pp. 213-235.
Michael Karst et al., Humidity & Temperature Sensors in Mobile Phones, Apr. 18, 2012, Sensirion AG, Switzerland.
Section 41.32-Bit Programmable Cyclic Redundancy Check (CRC), 2009, Microchip Technology Inc., DS39729A pp. 41-1-41-22.
D. Weiler et al., An Absolute Air Pressure Smart Sensor Family with 2 Dimensional Calibration, XP031895684, pp. 254-257.
Zhengjun Li, "Design of Intelligent Node of Can Bus Based Distributed Measuring and Control System", Process Automation Instrumentation, vol. 24, No. 6, pp. 25-28, Jun. 30, 2003.
Chinese Office Action relating to application No. 201510451461.5, dated Nov. 2, 2018.
Chinese Office Action relating to application No. 201510451461.5, dated Sep. 2, 2019.

\* cited by examiner

OTP contents:
```
1:      0x0500      // 5 x-intv, 0 y-intv
2:      0x1233      // interval i0
3:      0x44AB      // interval i1
4:      0x3001      // interval i2
5:      0x1231      // interval i3
6:      0xAB13      // sampling point S0
7:      0x1235      // sampling point S1
...
11:     0xAAAF      // sampling point S5
```

OTP contents:
```
1:      0x0003      // 0 x-intv, 3 y-intv
2:      0x1233      // interval i0
3:      0x44AB      // interval i1
4:      0xAB13      // sampling point S0
5:      0x1235      // sampling point S1
6:      0x1235      // sampling point S2
7:      0xAAAF      // sampling point S3
```

```
OTP contents:
1:      0x0100      // 1 x-intv, 0 y-intv
2:      0xAB13      // sampling point S0
3:      0x1235      // sampling point S1
```

SENSOR CHIP

TECHNICAL FIELD

The present invention relates to a sensor chip and to a method of processing a sensor signal in a sensor chip.

BACKGROUND ART

Sensors tend to become integrated into chips which chips at the same time provide processing means for processing signals supplied by the sensors.

DISCLOSURE OF THE INVENTION

The problem to be solved by the present invention is to provide a sensor chip that facilitates an adaptation of the processing, e.g. for new variants of the sensor chip, without the need to conduct a full mask redesign.

This problem is solved by a sensor chip according to the features of claim 1.

The sensor chip comprises a sensing element for sensing a measure. For example, the sensing element may be a sensing element for one of sensing a flow of a fluid such as a gas or a liquid, or for sensing a pressure, or for sensing humidity, or for sensing a gas, which list, is not limited. The sensor element may provide a sensor signal, e.g. in analogue form which preferably is converted into digital sensor values by an analogue to digital converter. In another embodiment, the sensing element may directly provide digital sensor values.

The sensor element may be arranged on or integrated into a chip which chip is referred to as sensor chip. The chip preferably contains an integrated circuit in addition to the sensor element, e.g. for processing the sensor signal. The sensor chip preferably comprises a substrate, such as a semiconductor substrate, and preferably a silicon substrate, and material layers thereon such as insulation and/or metal layers, for integrating the circuitry to.

The sensor chip further contains an on-chip memory, which on-chip memory preferably is a non-volatile memory, and preferably is an at least one-time programmable memory, which memory is also integrated into the chip. In this on-chip memory, a configuration of a look up table of dimension N is stored for assigning an output value to a combination of N input values. In another embodiment additional one or more look up table configurations are stored in the on-chip memory, either of the same dimension N or of a different dimension.

The or each look up table configuration includes a look up table header including information indicating a number of sampling points for each dimension N. A sampling point represents as input value in a dimension for which input value an output value is stored in the look up table for each sampling point of the other dimensions. In view of space restrictions, it may not be feasible to store output values for all possible input values. Hence, only a couple of input values are selected for which output values are stored in the look up table configuration. For input values in between two sampling points, an interpolation technique may be applied for determining a corresponding output value.

Instead of storing the number of sampling points itself per dimension, a number of sampling point intervals may be stored per dimension. Preferably, the or each look up table header additionally includes information referring to an interpolation to be applied per dimension for determining an output value for an input value that does not match any one of the sampling points in this dimension. Specifically, an order of such interpolation may be stored in the look up table header.

In addition to the look up table configuration header, it is preferred that the or each look up table configuration includes an interval size between two adjacent sampling points per dimension which one or more sizes are stored in the on-chip memory given that the intervals between different sampling points may not necessarily be equidistant. Finally, it is preferred that for the or each look up table configuration the output values for each combination of sampling points of the various dimensions are stored in the on-chip memory.

In many applications, it is desired to process and hence modify sensor signal values in sequence for different purposes. In such scenario, it is preferred to apply multiple different look up table configurations in sequence, wherein specifically an output value of a first of the look up table configurations represents an input value to a second of the look up table configurations. For example, a sensor signal value may undergo a transformation on-chip including a linearization procedure, a calibration procedure, a temperature compensation procedure, etc., each of which transformations of the sensor signal may be realized by applying a dedicated look up table configuration.

An engine initiating the application of a sequence of look up table configurations preferably is a system controller of the sensor chip which operates a system bus and copies data thereto and fetches data therefrom. A corresponding program for processing different look up table configurations in sequence may be a micro program which causes the system controller to call the different look up tables when being interpreted by the system controller by copying a memory address the look up table configuration can be found at in the on-chip memory via the system bus to a look up table engine. The look up table engine, which preferably contains hardwired registers and which preferably only can execute additions, may via the memory address get access to the subject look up table configuration and copy the relevant data into its registers. After having received input values copied by the system controller to the look up table engine via the system bus, the look up table engine executes the determination of an output value in response to the supplied input values. The micro program to be interpreted by the system controller preferably is understood as a program containing hardware level instructions.

In one embodiment, all look up table configurations are of the same dimension N, specifically with N=2. In case one of the look up table configurations of a sensor chip requires only a single dimension, the number of sampling points of one of the dimension is set to zero.

Hence, a sensor chip according to the embodiments introduced allows the processing of a sensor signal such as on-chip linearization and on-chip temperature compensation. This is implemented by means of one or more look-up tables stored in an on-chip memory, such as an OTP, an EEPROM, a RAM, etc., thereby eliminating the need for a complex and costly arithmetic logic unit (ALU). In particular, the configuration of a look-up table is not hard-coded in the digital part of the sensor chip. Instead, the look up table configuration is preferably stored in the on-chip memory preferably including look up table header and output values. The look up table header is decoded by on-chip logic, e.g. in the look up table engine, to extract the required information about the look-up table. Hence, the configuration of the look-up table preferably includes a number of sampling points per dimension, a position of the sampling points, and the corresponding output values are no longer hard coded in the digital part of the sensor chip but are stored in the on-chip memory. In addition, it is preferred that processing steps, e.g. calling different look up tables stored in the on-chip memory in sequence are no longer hard-coded but are stored in form of a micro-program (macro) in the on-chip memory and are executed by the system controller of the sensor chip. On the other hand, the determination of the output values is not based on a mathematical approach as would be feasible when using a full scale microprocessor. A microprocessor instead would require a large scale chip size which is not available in small scale sensor chips. Since no main memory is required either, chip size can be saved on this end, too. In one embodiment, the look up table engine solely operates on registers and busses, and it is preferred that the look up operations are executed solely by applying additions e.g. by means of shifting registers but no multiplications or other higher order operations. The look up table configuration can be allocated in the on-chip memory where desired.

Summarizing, a reuse of a data processing unit in a sensor chip for new projects is no longer limited by the tremendous effort of re-masking the chip for implementing new look up tables and/or new processing sequences of such look up tables. Now, changes in a data path and/or a look up table can be accomplished without a full mask redesign. Without the need of a new tape-out, the following parameters of a sensor chip can preferably be changed:

The number of look-up tables
The configuration of a look-up table
A data path/processing sequence of look-up tables
Sample points of the look-up tables
The location of look-up tables in on-chip memory, in view of optimizing the memory usage.

It is preferred, that a look up table configuration requires one or more discrete input values and in response supplies a discrete output value. Hence, it is desired to apply a sensor value in digital form as one of the one or more input values to the look up table. In this context, a sensor value shall not only encompass the sensor value at the output of an analogue to digital converter if any, or at the sensing element output, but shall also include sensor values that are already modified according to one or more of the look up table configurations. Hence, an output value of a look up table may also be considered a sensor value, i.e. this output value is a sensor value derived from the sensor value originally supplied by the sensing element or the analogue to digital converter.

In a one dimensional look up table configuration the sensor value may be the one input value that is mapped to a corresponding output value. However, in a two- or more dimensional look up table configuration, at least one other input value is applied such that the look up table provides an output value that is defined for this particular combination of two input values.

The one or more other input values may include an operational value of the device, such as heater current or heating time value, etc., or may be include another sensor value supplied by another sensing element, which other sensor preferably is also arranged on or integrated into the sensor chip. Such other sensor may, for example, be a temperature sensor, and/or a humidity sensor which sensors are provided for compensating temperature and/or humidity induced deviations in the sensor signal of the origin sensing element. In this respect, a look up table for a temperature compensation configured for this purposes may include two dimensions and expects two input values, i.e. a sensor value and a temperature value in response to which input values the look up table provides an output value that represent a temperature compensated sensor value. In case the other sensing element provides its sensor signal in analogue form, another analogue to digital converter may be arranged on the chip for converting the other sensor signal from its analogue form into a series of other sensor values in digital form. After conversion, each digital sensor signal or other sensor signal may be temporarily stored in an assigned register and be fetched from there by the system controller for applying the respective sensor value as input value to a look up table configuration. However, in another embodiment he or any other input signal may also be supplied from outside the sensor chip, and specifically may be an input value representing a sensor value from a sensor outside the sensor chip.

According to another aspect of the present invention, a method is provided for processing a sensor signal in a sensor chip. A sensing element of a sensor chip senses a measure and provides a sensor signal. From the sensor signal, a sensor value is derived, and input value to a configuration of a look up table of dimension N stored in an on-chip memory of the sensor chip for assigning an output value to a combination of N input values. By making use of the look up table corresponding to the look up table configuration, an output value is generated dependent on the supplied sensor value and possible dependent on other values.

It is noted that embodiments described in relation to one category of claims shall be considered as disclosed in connection with the one or more other category, too.

Other advantageous embodiments are listed in the dependent claims as well as in the description below.

BRIEF DESCRIPTION OF THE DRAWINGS

The embodiments defined above and further aspects, features and advantages of the present invention can also be derived from the examples of embodiments to be described hereinafter and are explained with reference to the drawings. In the drawings the figures illustrate in FIG. 1 a block diagram of a sensor chip according to an embodiment of the present invention, FIG. 2 a flow of information between two building blocks of a sensor chip according to an embodiment of the present invention, FIG. 3-6 look up table configurations as used in one or more sensor chips according to preferred embodiments of the present invention, including graphical representations of such look up table configurations for illustration purposes, and FIG. 7 a flowchart of a method according to an embodiment of the present invention.

DETAILED DESCRIPTION OF THE DRAWINGS

Figure 1:
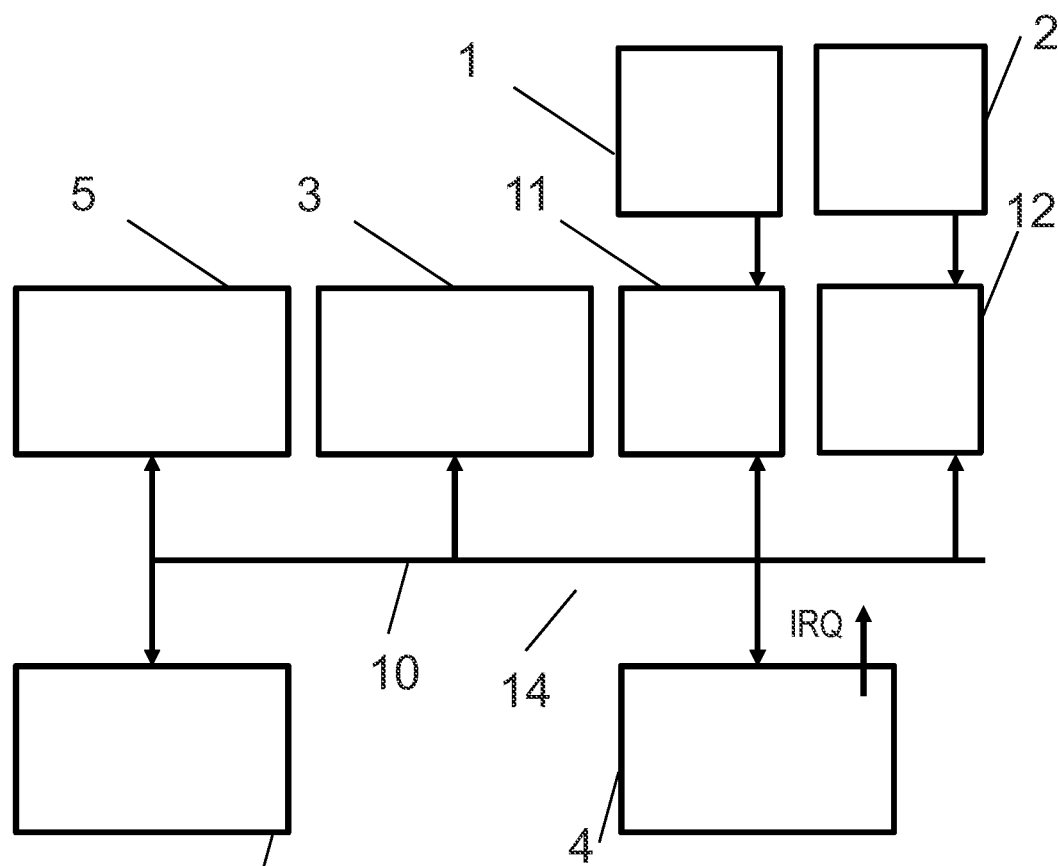

Same or similar elements are referred to by the same reference numerals across all Figures.

FIG. 1 illustrates a block diagram of a sensor chip according to an embodiment of the present invention. The sensor chip contains a bus 10 which interconnects various elements of the sensor chip. In the present embodiment, an one-time programmable on-chip memory 3 is provided and connected to the bus 10 as are two analogue to digital converters ADC 11 and 12, each of which converting an analogue sensor signal of a sensor into a series of digital sensor values. One of the sensors is a flow sensor 1 but could be any other sensor, the other one is a temperature sensor 2. In the on-chip memory 3, preferably one or more look up table configurations are stored each containing a configuration of a corresponding look up table such as its dimension etc., and its output values that are assigned to one or more input values. A unit 4 referred to as look up table execution preferably is implemented in hardware logic and preferably comprises registers for executing operations on look up tables. Preferably, the unit 4 provides only hardwire logic for adding values in registers and being incapable of executing higher order operations such as multiplications etc. The execution of a look up operation may preferably be implemented as follows:

A system controller 5 may trigger the lookup operation and send a header address to the look up table engine 4 which header address is the memory address at which the desired look up table configuration can be found in the on-chip memory 3. By receiving this header address, the look up table engine 4 gets access to the on-chip memory 3 and the requested look up table configuration that resides at the respective header address.

In one embodiment, the look up table engine 4 may copy the relevant information from the look up table header into local registers. The system controller 5 may fetch sensor signal values from registers of the analogue to digital converters 11, 12 that shall serve as input values to the look up table, and may store these values in registers of the look up table engine 4.

The next steps are preferably performed in the look up table engine 4: The input values are evaluated in their position relative to sample values of the respective dimension, and the closest sample values are identified per dimension. An interpolation routine is applied to the input values according to the interpolation requested by the look up table header. Finally, an output value is determined and stored to a register of the look up table engine, wherefrom the system controller 5 may pick it up and transfer to the interface 6, for example.

In another embodiment of the present invention, the look up table 4 and the on-chip memory 3 have a dedicated interface between these two units in order to reduce the workload on the bus 10.

In a preferred embodiment, a data flow from and to the look up table engine 4 is controlled entirely by the system controller 5, except, e.g. where there is a direct link between the look up table engine 4 and the on-chip memory 3.

Hence, the system controller 5 is configured to fetch sensor signal values from the registers of the analogue to digital converters 11 and 12 and provide them alone or in combination to the look up table engine 4. Results from looking up the respective look up table configurations may temporarily be stored in a buffer and may in one example be input to another look up table configuration where another output value may be looked up for the respective one or more input values which output value may then, for example, be copied over the bus 10 to an interface 6, such as an I$^2$C interface, to make this processed sensor value available to the outside of the sensor chip.

The system controller 5 preferably controls the fetching of input values from registers, triggering the look up table operations in the look up table engine 4 with these input values, and storing and/or forwarding the output values from the look up table engine 4. For doing so, a micro program preferably is stored in the on-chip memory 3, which micro program is executed by the system controller 5.

Figure 2:
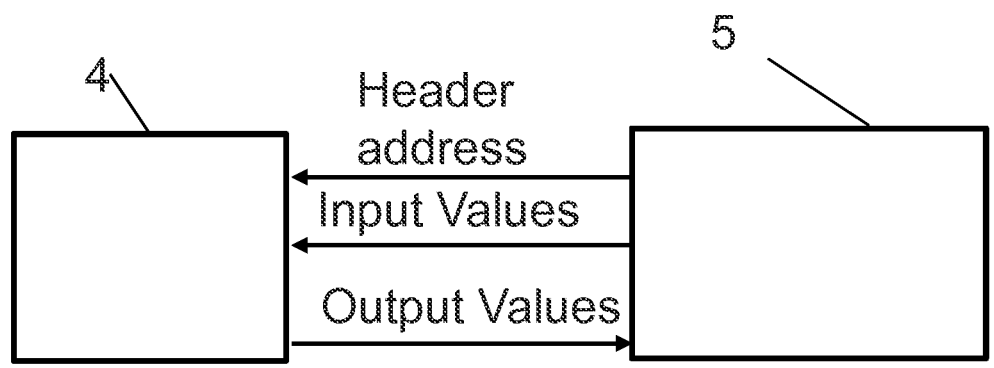

FIG. 2 illustrates a flow of information between two building blocks of a sensor chip according to an embodiment of the present invention, i.e. between the look up table engine 4 of FIG. 1, and the system controller 5 of FIG. 1 that interprets a micro program for controlling the look up table operations. First, in response to a trigger, a header address is identified for the on-chip memory at which the desired look up table configuration resides/starts. The look up table engine 4 receives this header address and gets access to the look up table configuration in the on-chip memory. Then, input values that shall be applied to the selected look up table configuration are provided to the look up table engine 4. When the look up table engine 4 has determined an output value for the supplied input values, this output value is copied by the system controller 5 to the on-chip memory 5, or is copied to an interface 6.

Figure 3:
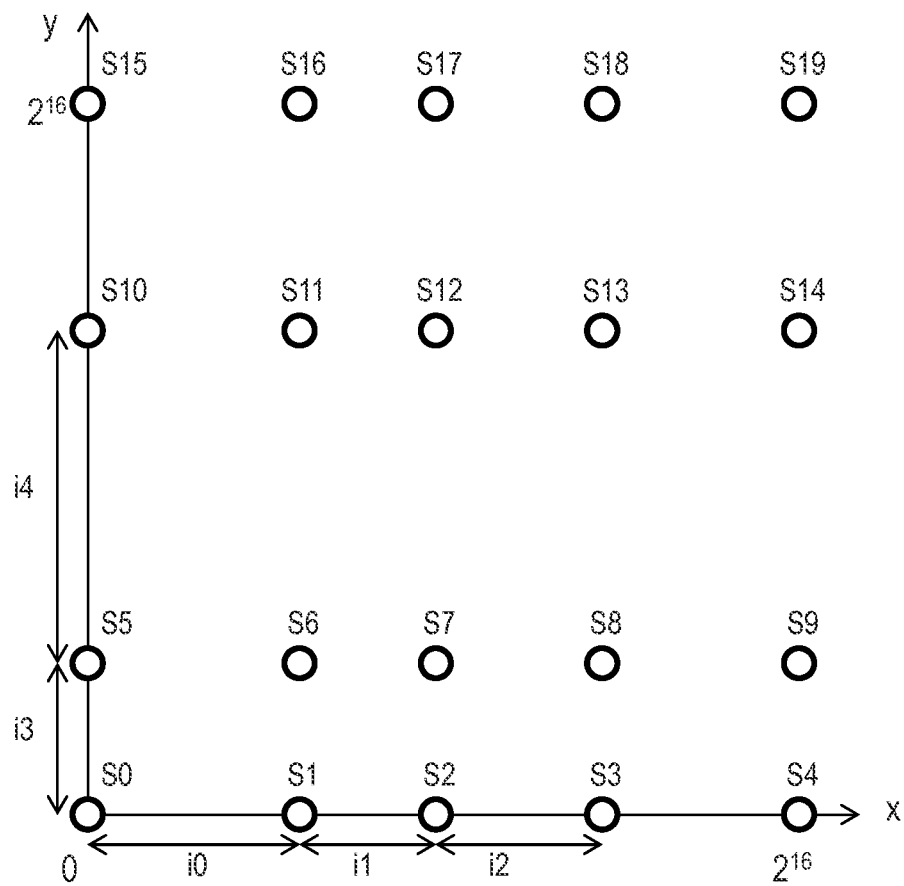

FIG. 3 shows a look up table configuration of dimension N=2 as used in a sensor chip according to a preferred embodiment of the present invention.

In the lower section, a sample description of the two dimensional look up table is shown as is stored in the on-chip memory, which in the present example is a one-time programmable (OTP) on-chip memory.

The first word that is stored in the OTP, i.e. word "1:" in the first line, describes the basic configuration of the look up table, and is also referred to as look up table header. In the present example, four items of information are defined in the look up table header and are encoded by the four-digit hexadecimal number, that is flagged by "0x". Note that the hexadecimal values are finally binary encoded: Each digit with a hexadecimal value is encoded by four binary bits. Hence, the four digits for hexadecimal values are transformed into sixteen bits of binary values. In the present embodiment, the number of intervals in y dimension is encoded in bits 0 to 6. In the present example, three intervals are encoded in y dimension represented by the sequence "000011" in the binary representation, and "3" in the hexadecimal representation. Bit 7 indicates the order of interpolation applied in y dimension. Value "0" indicates linear interpolation, while value "1" indicates a quadratic interpolation. Since bit 7 in the present example takes the value "0"—the value in the second hexadecimal digit is "0", too, given that the bits 4 to 6 remain "0" from the encoding of the number of intervals in y dimension. The bits 8 to 14 are used for encoding the number of intervals in x dimension which presently is four. This results in the hexadecimal value "4" in the third digit in the hexadecimal representation. Finally, the last bit 15 indicates the interpolation in x dimension to be applied, which in the present example is a quadratic interpolation encoded as "1" in the binary representation. Since the other binary digits 14, 13 and 12 are all "0" from the interval encoding, the binary digits 15 to 12 read [1,0,0,0], which is "8" is the hexadecimal representation.

The words "2:" to "26:" stored in the OTP relate to the look up table values and the input values they are assigned to. The number and arrangement of these words depends on the configuration of the look up table as defined in the first word "1:". Under the assumption that the first sample point of any dimension is at "0", while the last sample point is at $2^{16}$, a size of only x−1 intervals need to be addressed provided x sample points are indicated in the look up table header. The same holds for the y dimension, resulting in only three intervals to be sized for the x dimension, which are written to the on-chip memory by words "2:", "3:" and "4:", while for the y dimension only two intervals need to be written to the on-chip memory by words "5:" and "6:".

In the remaining words "7:" to "26:" the output values are stored for each combination of sample values in x and y dimension. For example, if the input values match the sample values S4 and S15, the output value of sample values (S4, S15)=S19 is FFFE" according to word "26:". In case an output value is requested from the look up table for one or more input values that do not exactly match one of the sampling points on the x- or y-axis, an interpolation is applied in one or more of the x and the y dimension according to the order of interpolation as written to the first word "1:".

In the upper graphical section of FIG. 3, the look up table as defined by the below instructions in the OTP on-chip memory is graphically illustrated.

Figure 4:
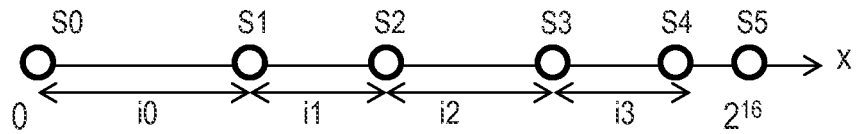

FIG. 4 shows a different look up table configuration of dimension N=2 as used in a sensor chip according to a preferred embodiment of the present invention, and for which look up table the same convention for the look up table header is applied as for the look up table header in FIG. 3. According to the lower section which again is a sample description of the look up table configuration, and specifically according to word "1:", the x dimension has five sample values while the y dimension has no sample values. Hence, the basic N=2 table dimension is reduced to a one dimensional look up table in x dimension by setting the number of sample points in the y dimension to zero. Linear interpolation is applied in x dimension. The words "2:" to "5:" contain the interval sizes between the sample points in x dimension, while in words "6:" to "11:" the output values are given.

Again, in the upper graphical section, the look up table as defined by the below instructions in the OTP on-chip memory is graphically illustrated.

Figure 5:
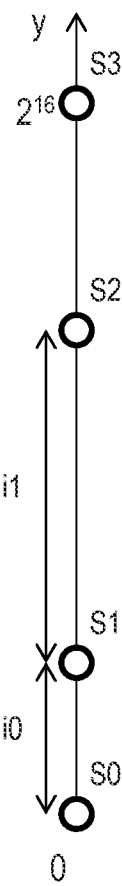

FIG. 5 shows a different look up table configuration of dimension N=2 as used in a sensor chip according to a preferred embodiment of the present invention, and for which look up table the same convention for the look up table header is applied as for the look up table header in FIG. 3. According to the lower section which again is a sample description of the look up table configuration, and specifically according to word "1:" the y dimension has three sample values while the x dimension has no sample values. Hence, the basic N=2 table dimension is reduced to a one dimensional look up table in y dimension by setting the number of sample points in the x dimension to zero. Linear interpolation is applied in y dimension. The words "2:" and "3:" contain the interval sizes between the sample points in y dimension, while in words "4:" to "7:" the output values are given.

Again, in the upper graphical section, the look up table as defined by the below instructions in the OTP on-chip memory is graphically illustrated.

Figure 6:
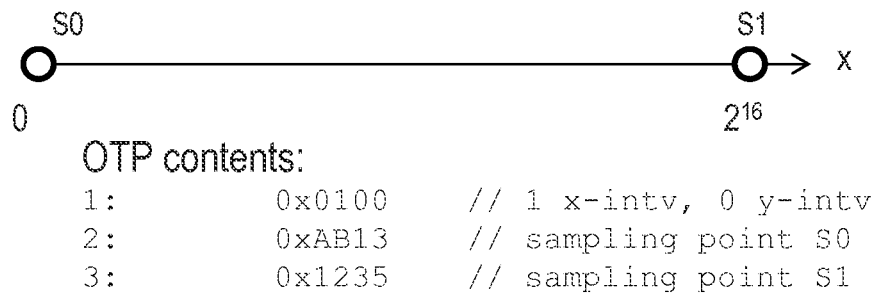

FIG. 6 shows a different look up table configuration of dimension N=2 as used in a sensor chip according to a preferred embodiment of the present invention, and for which look up table the same convention for the look up table header is applied as for the look up table header in FIG. 3. According to the lower section which again is a sample description of the look up table configuration, and specifically according to word "1:", the y dimension has only two sample values while the x dimension has no sample values. Hence, the basic N=2 table dimension is reduced to a one dimensional look up table in x dimension by setting the number of sample points in the y dimension to zero. Linear interpolation is applied in x dimension. The words "2:" and "3:" contain the output values, while no interval sizes are required.

Again, in the upper graphical section, the look up table as defined by the below instructions in the OTP on-chip memory is graphically illustrated.

Figure 7:
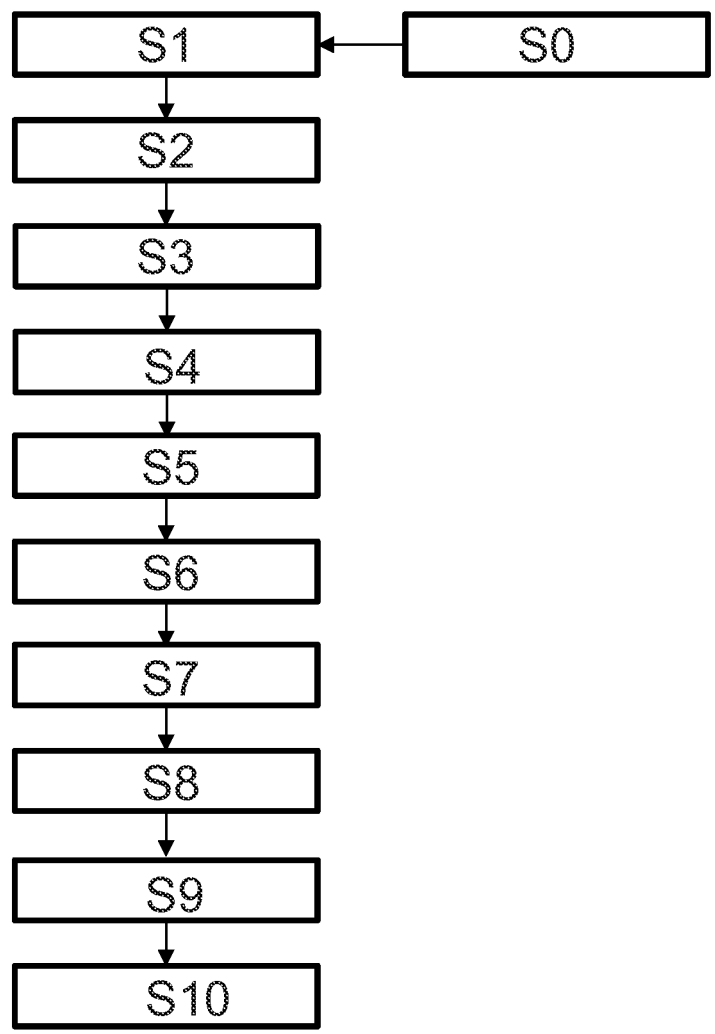

FIG. 7 shows a flowchart of a method according to an embodiment of the present invention. In the present example, it is desired to process a flow sensor signal and compensate for the impact of temperature. It is assumed that the sensing element provides an analogue flow sensor signal which is analogue to digital converted first into a series of digital flow sensor values.

In step S0 the processing is started. In step S1, a flow sensor value—which may also be referred to as raw data at this stage—is copied as input value from the analogue to digital converter to a look up table engine. The look up table engine applies a first look up table configuration which provides an output value that is flow offset/gain corrected over the input value. The look up table configuration preferably allows looking up values in only one dimension, i.e. for each input, value an output value is assigned. For each specific input flow sensor value applied to this look up table configuration, a resulting output flow sensor value is determined in step S2 and is copied to a temporary buffer in step S3.

It is assumed that the other sensing element in form of a temperature sensor provides an analogue temperature sensor signal which is analogue to digital converted first into a series of digital temperature sensor values. In step S4, such temperature sensor value is copied from the assigned analogue to digital converter as input value to the look up table engine now applying a second look up table configuration which provides an output value that is temperature offset/gain corrected over the input values. The look up table configuration preferably allows looking up values in only one dimension. For each specific input temperature sensor value applied to this second look up table configuration, a resulting output temperature sensor value is determined in step S5 and is copied to a temporary buffer in step S6.

In step S7, the output temperature sensor value resulting from step S6 is copied to from the temporary buffer to the look up table engine now applying a third look up table configuration with two dimensions, as is the output flow sensor value resulting from step S3. With these two signal values as input values to the third look up table, the output value of the third look up table is an offset and temperature compensated flow sensor value, which may be copied to an interface, such as the I2C interface, for output.

While there are shown and described presently preferred embodiments of the invention, it is to be distinctly understood that the invention is not limited thereto but may be otherwise variously embodied and practiced within the scope of the following claims.

The invention claimed is:
1. Sensor chip, comprising
a sensing element providing a sensor signal,
an on-chip memory,
a configuration of a look up table of dimension N stored in the on-chip memory for assigning an output value to a combination of N input values,
a look up table engine for determining a corresponding output value in response to receiving a memory address for the look up table configuration and in response to receiving a sensor value derived from the sensor signal as one of the N input values,
a system controller configured to copy the memory address and the sensor value as one of the N input values to the look up table engine for generating the corresponding output value,
wherein the look up table engine is implemented as hardware,
different configurations of look up tables of dimension N stored in the on-chip memory each for assigning an output value to a combination of N input values, wherein the system controller is configured to call the different look up tables in sequence,
wherein calling different look up tables is stored in form of a micro-program in the on-chip memory, and is executed by the system controller.

2. Sensor chip according to claim 1,
wherein an output value of a first of the look up table configurations represents an input value to a second of the look up table configurations.

3. Sensor chip according to claim 1,
wherein a program that makes the different look up table configurations be called in sequence when being interpreted by the system controller is stored in the on-chip memory, and
in particular wherein the program is a micro program.

4. Sensor chip according to claim 1,
wherein the on-chip memory is a one-time programmable on-chip memory.

5. Sensor chip according to claim 1,
wherein the or each look up table configuration includes a look up table header comprising information with respect to a number of sampling points for each dimension N, a sampling point representing an input value in the corresponding dimension for which input value an output value is stored in the look up table configuration for each sampling point of any of the other dimensions, and
in particular wherein the information with respect to the number of sampling points comprises a number of sampling point intervals between the sampling points in the corresponding dimension.

6. Sensor chip according to claim 5
wherein the or each look up table header includes information referring to an interpolation to be applied per dimension for determining an output value for an input value in this dimension that does not match any one of the sampling points, and
in particular wherein the information referring to the interpolation includes an order of interpolation to be applied.

7. Sensor chip according to claim 1,
wherein N=2 for each look up table configuration, and
wherein a look up table configuration of a single dimension is implemented by setting the information with respect to the number of sampling points for the other dimension to zero.

8. Sensor chip according to claim 1,
wherein the or each look up table configuration indicates an interval size between two adjacent sampling points for each dimension N.

9. Sensor chip according to claim 1,
wherein the or each look up table configuration includes an output value for each combination of sampling points of the various dimensions.

10. Sensor chip according to claim 1, comprising
an analogue to digital converter for converting the sensor signal from an analogue form into a series of sensor values in digital form,
a register for temporarily storing the sensor values.

11. Sensor chip according to claim 1, comprising
another sensing element providing another sensor signal,
another analogue to digital converter for converting the other sensor signal from an analogue form into a series of other sensor values in digital form,
another register for temporarily storing the other sensor values.

12. Sensor chip according to claim 11,
wherein the other sensing element is one of a temperature sensor and a humidity sensor for compensating temperature or humidity dependent signal variations in the sensor signal, and
wherein the sensing element is one of a
a flow sensor;
a humidity sensor;
a gas sensor;
a pressure sensor.

13. Sensor chip according to claim 1,
wherein following parameters of the sensor chip are changeable:
the number of look-up tables,
the configuration of a look-up table,
a data path/processing sequence of the look-up tables,
sample points of the look-up tables,
the location of the look-up tables in the on-chip memory.

14. Sensor chip, comprising
a sensing element providing a sensor signal,
an on-chip memory,
a configuration of a look up table of dimension N stored in the on-chip memory for assigning an output value to a combination of N input values, the configuration of the look-up table including a number of sampling points per dimension, a position of the sampling points, and output values, and
a look up table engine for determining a corresponding output value in response to receiving a memory address for the look up table configuration and in response to receiving a sensor value derived from the sensor signal as one of the N input values,
a system controller configured to copy the memory address and the sensor value as one of the N input values to the look up table engine for generating the corresponding output value,
wherein the look up table engine is implemented as hardware,
different configurations of look up tables of dimension N stored in the on-chip memory each for assigning an output value to a combination of N input values,
wherein the system controller is configured to call the different look up tables in sequence,
wherein calling different look up tables is stored in form of a micro-program in the on-chip memory, and is executed by the system controller.

15. Sensor chip according to claim 14,
wherein following parameters of the sensor chip are changeable:
the number of look-up tables,
the configuration of a look-up table,
a data path/processing sequence of the look-up tables,
sample points of the look-up tables,
the location of the look-up tables in the on-chip memory.

16. Method for processing a sensor signal in a sensor chip, comprising
sensing a measure by means of a sensor element of the sensor chip,
deriving a sensor value from the sensor signal,
receiving a memory address for a configuration of a look up table, applying the sensor value and the memory address as input values to the look up table configuration of dimension N stored in an on-chip memory of the sensor chip for assigning an output value to a combination of N input values, thereby generating the corresponding output value.

* * * * *